United States Patent [19]

Tur

[11] Patent Number: 4,844,884
[45] Date of Patent: Jul. 4, 1989

[54] COSMETIC SUNSCREEN PRODUCT FOR THE FACE AND BODY

[75] Inventor: Wladimir Tur, Mutschellen, Switzerland

[73] Assignee: Induchem AG, Dubendorf, Switzerland

[21] Appl. No.: 113,005

[22] Filed: Oct. 23, 1987

[30] Foreign Application Priority Data

Dec. 3, 1986 [CH] Switzerland .................... 4819/86

[51] Int. Cl.⁴ .................... A61K 7/021; A61K 7/42
[52] U.S. Cl. .................................................. 424/59
[58] Field of Search ........................................ 424/59

[56] References Cited

U.S. PATENT DOCUMENTS

| 3,937,804 | 2/1976 | Delaney et al. | 424/52 |
| 3,937,809 | 2/1976 | Jacobi | 424/60 |
| 4,021,538 | 5/1977 | Yu et al. | 424/60 |
| 4,419,343 | 12/1983 | Pauly | 424/59 |
| 4,515,773 | 5/1985 | Herlihy | 424/59 |

FOREIGN PATENT DOCUMENTS

| 117080 | 8/1984 | European Pat. Off. . |
| 964172 | 5/1957 | Fed. Rep. of Germany . |
| 1617590 | 6/1971 | Fed. Rep. of Germany . |
| 7004557 | 11/1971 | France . |
| 7513420 | 4/1977 | France . |
| 642537 | 4/1984 | Switzerland . |

Primary Examiner—W. J. Shine
Attorney, Agent, or Firm—James E. Nilles

[57] ABSTRACT

Cosmetic sunscreen products which contain a tyrosine derivative of the formula:

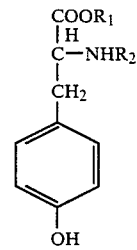

in which $R_1$ is H or $CH_3-(CH_2)_x$, with X being 1 to 20, and $R_2$ is $CH_3CO-$ or $CH_3-(CH_2)_y-CO$, with Y being 1 to 20, provide a long lasting and dark, natural tan after a short exposure to sunlight. The sunscreen product may contain an activator which is an alkali metal or alkaline earth metal salt of adenosine-5'-tri-, di-, or monophosphoric acid and mixtures thereof with an alkali metal or alkaline earth metal hydrogen phosphate.

31 Claims, 1 Drawing Sheet

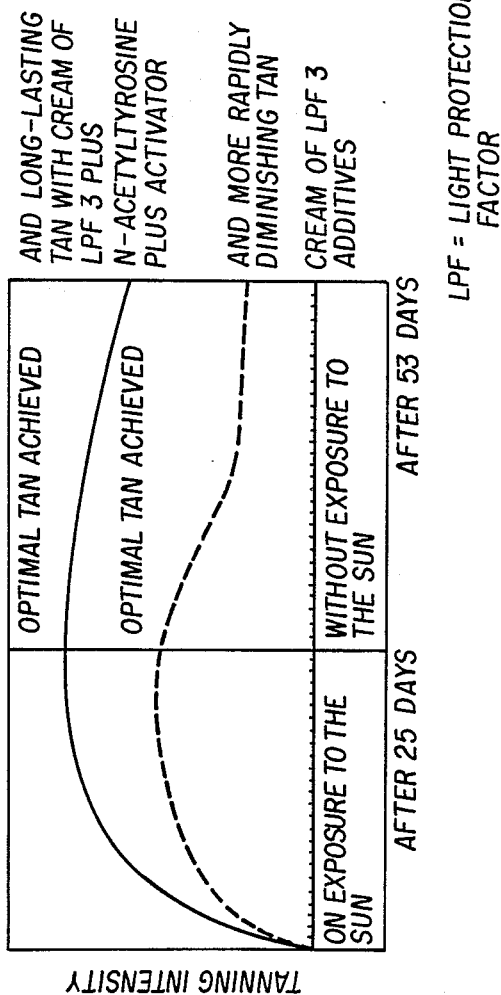

COSMETIC SUNSCREEN PRODUCT FOR THE FACE AND BODY

BACKGROUND OF THE INVENTION

Cosmetic sunscreen products have the object, chiefly owing to the content of suitable UV filters, of protecting the skin from sunburn. However, the efficiency of the protection is inversely proportional to the tanning which is achieved, that is to say the greater the protection the less the tanning of the skin.

It remains the desire of every sunbather to achieve, after the shortest possible exposure to the sun, the optimal, dark, long-lasting and natural tanning of the skin.

The present invention has the object of providing a cosmetic sunscreen product which, in addition to the customary protection from radiation by UV filters, and the skin-care properties of the product base, allows, on exposure to the sun, more rapid, darker, more persistent and biologically natural tanning of the skin than do known products of this type.

Extensive research into skin pigmentation has shown that rapid, dark and persistent tanning of the skin depends not on the number of pigment-forming cells but on the efficiency of the metabolic processes in the pigment cells of the skin.

It is known that the skin pigment melanin is produced in the skin from tyrosine, an amino acid. This conversion of tyrosine takes place by an oxidative bioreaction under the influence of light, heat and oxygen. This reaction, that is to say the transfer of oxygen to tyrosine, is made possible in the skin by an enzyme, tyrosinase.

Based on this known biological process, it was obvious to add to sunscreen products tyrosine, the starting substance for the formation of melanin, in the hope that, by this means, there would be more intense tanning on sunbathing. This has now been attempted, but it emerged that it was possible to achieve only a slight intensification of tanning by this addition. It is not possible to add the enzyme tyrosinase, which occurs in the skin, as activator to the tyrosine-containing sunscreen products now known, because the enzyme is difficult and costly to obtain and is chemically unstable. The intrinsic coloration exhibited by other activators now used is unfavorable.

SUMMARY OF THE INVENTION

Hence, the object of the invention is to eliminate the stated disadvantages of the slight intensification of tanning, the instability and/or the intrinsic coloration of the sunscreen products now known.

DESCRIPTION OF THE DRAWING

The drawing is a curve plotting tanning intensity against exposure to the sun and without exposure to the sun.

DESCRIPTION OF THE PREFERRED EMBODIMENT

In the search for suitable stable tyrosine derivatives which are readily soluble in water or readily soluble in oil and which, applied to the skin, rapidly penetrate into the skin and are oxidized to melanin, surprisingly the following suitable derivatives of tyrosine, of the following formula:

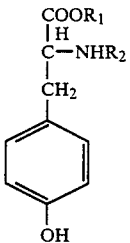

in which $R_1$ is H or $CH_3-(CH_2)_x$, with x being 1, 2, ... 20, and $R_2$ is $CH_3CO$ or $CH_3-(CH_2)_yCO$, with y being 1, 2, ... 20, have been found.

In this connection, the following tyrosine derivatives have proved to be particularly suitable:
N-acetyltyrosine
N-acetyltyrosine ethyl ester
N-myristoyltyrosine
N-myristoyltyrosine myristyl ester
N-palmitoyltyrosine
N-palmitoyltyrosine palmityl ester
N-stearoyltyrosine
N-stearoyltyrosine stearyl ester.

In contradiction of the prevailing scientific opinion, which has classified some of these substances as potent inhibitors of tyrosinase activity, that is to say of melanin formation, they result, with suitable activators, on the contrary in more intense tanning.

In the search for suitable activators which can be applied to the skin with the abovementioned tyrosine derivatives and can rapidly convert, under the influence of sunlight, the tyrosine derivatives into melanin, the adenosine compounds and/or mixtures of the following formulae have been found, likewise surprisingly:

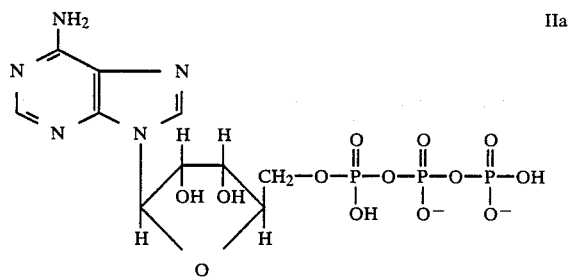

$2 AK^+$ or $EAK^{2+}$ (ATP salt)

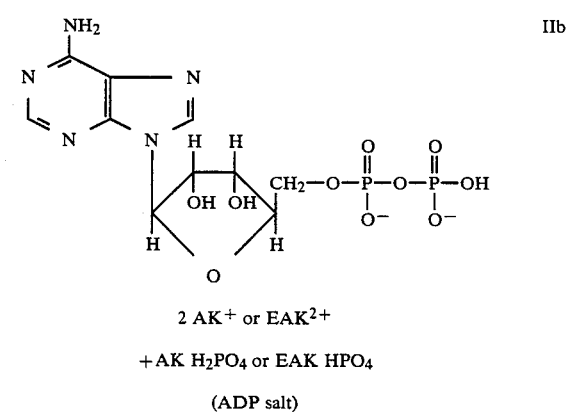

$2 AK^+$ or $EAK^{2+}$ $+ AK\ H_2PO_4$ or $EAK\ HPO_4$ (ADP salt)

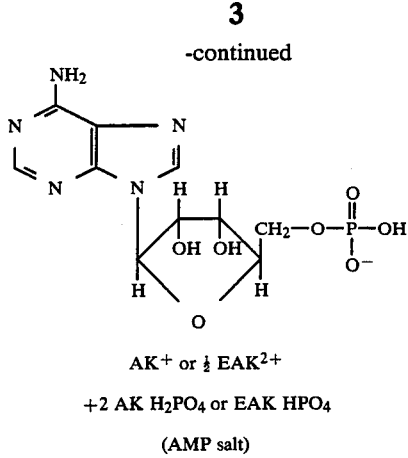

AK⁺ or ½ EAK²⁺

+2 AK H$_2$PO$_4$ or EAK HPO$_4$ (AMP salt)

in which AK is an alkali element and EAK is an alkaline earth element, and/or a butyl ester of an adenosine-5′-phosphoric acid of the following formulae ATP di-n-butyl ester

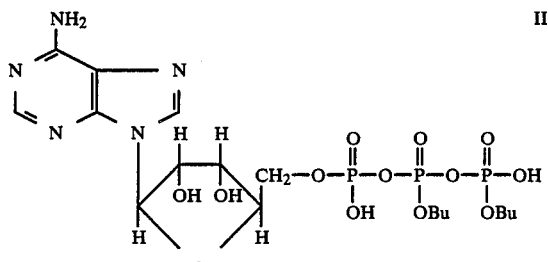

IIIa

ADP di-n-butyl ester

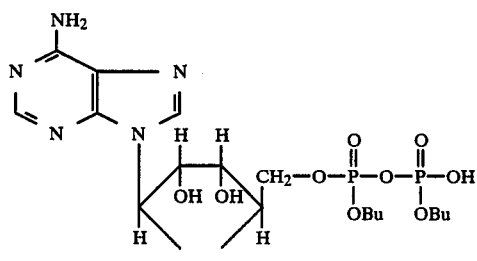

IIIb

AMP n-butyl ester

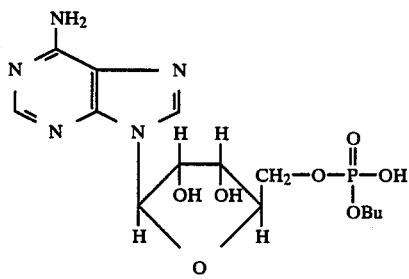

IIIc

Bu being butyl.

In this connection, the following adenosine compounds have proved to be particularly suitable: adenosine-5′-triphosphoric acid disodium salt and the mixture of adenosine-5′-diphosphoric acid disodium salt and sodium hydrogen phosphate in the mixing ratio by weight of 4:1, and a mixture of adenosine-5′-monophosphoric acid sodium salt and sodium hydrogen phosphate in the molar ratio 1:2, it being possible in all the abovementioned salts for lithium, potassium or magnesium also to be preferred in place of sodium, adenosine-5′-triphosphoric acid di-n-butyl ester,
adenosine-5′-diphosphoric acid di-n-butyl ester and
adenosine-5′-monophosphoric acid n-butyl ester.

Scientific opinion states that these abovementioned adenosine compounds also inhibit or prevent biological tanning.

Some of the tyrosine derivatives are substances which can be obtained commercially, otherwise they can be prepared in a straightforward manner by processes known in organic chemistry. Adenosine-mono-, di- and tri-phosphoric acid are likewise known substances from which it is possible to synthesize, in a straightforward manner, by known chemical preparation processes, the derivatives mentioned in the invention.

It has now emerged that, on sunbathing with the use of a sunscreen product which, in addition to a suitable UV filter and/or a mixture of the abovementioned tyrosine derivatives, contains one of the activators or a mixture thereof, it is possible more rapidly to achieve long-lasting and darker natural tanning of the skin. With the same product base and the same UV filter, but without the tyrosine derivative and activator, the onset of tanning is slower, the achieved intensity of tanning is significantly less, and the tan diminishes more rapidly in the course of time.

Comparative investigations on the human skin, with identical exposure to sun, have produced the following results:

Two products containing the same base (Example 1) were used. The first product contains only a UV filter, while the second product contains UV filter, tyrosine derivative and activator. The achieved intensities of tanning, which were measured continuously with an LF-90 color measuring apparatus from Dr. B. Lange, are shown by the diagram in the figure. This diagram shows that the second product containing UV filter, tyrosine derivative and activator allows the skin to achieve more intense and persistent tanning more rapidly. Thus, the addition, discovered here, of stable, colorless activators, in addition to stable, colorless tyrosine derivatives, permits optimal tanning of the skin, with minimal stress thereof, and differs in this way from the other known agents used for these purposes.

The additions of the tyrosine derivatives and adenosine compounds described in the invention which are necessary to achieve an optimal tanning with the sunscreen product according to the invention were determined, and the following values, for example, were found in this:

At least 0.3% by weight, preferably 0.4 to 5% by weight, in particular 1% by weight, of N-acetyltyrosine At least 0.4% by weight, preferably 0.4 to 5% by weight, in particular 1.5% by weight, of N-acetyltyrosine ethyl ester At least 0.3% by weight of a mixture of N-acetyltyrosine and N-acetyltyrosine ethyl ester At least 1.0% by weight, preferably 1.0 to 15.0% by weight, in particular 2% by weight, of N-myristoyltyrosine At least 1.0% by weight, preferably 1.0 to 15.0% by weight, in particular 3.0% by weight, of N-myristoyltyrosine myristyl ester At least 1.0, preferably 1.0 to 15.0% by weight, in particular 2.5% by weight, of N-palmitoyltyrosine At least 1.0, preferably 1.0 to 15.0% by weight, in particular 3.0% by weight, of N-palmitoyltyrosine palmityl ester At least 1.0% by weight, preferably 1.0 to 15.0% by weight, in particular 2.5% by weight, of N-stearoyltyrosine At least 1.0% by weight, preferably 1.0 to 15.0% by weight, in particular 3.0% by weight of N-stearoyltyrosine stearyl ester At least 0.01% by weight, preferably 0.01 to 1.0% by weight, in particular 0.05% by weight, of adenosine-5'-triphosphoric acid disodium salt At least 0.015% by weight of a mixture of adenosine-5'-monophosphoric acid sodium salt and sodium hydrogen phosphate in the molar ratio of 1:2

At least 0.015% by weight, preferably 0.015 to 1.0% by weight, in particular 0.06% by weight, of a mixture of adenosine-5'-diphosphoric acid disodium salt and sodium hydrogen phosphate in the mixing ratio by weight of 4:1

At least 0.015% by weight, preferably 0.015 to 1.0% by weight, in particular 0.06% by weight, of a mixture of adenosine-5'-monophosphoric acid sodium salt and sodium hydrogen phosphate in the mixing ratio by weight of 3:1

At least 0.02% by weight, preferably 0.02 to 1.5% by weight, in particular 0.08% by weight, of adenosine-5'-triphosphoric acid di-n-butyl ester At least 0.02% by weight, preferably 0.02 to 1.5% by weight, in particular 0.08% by weight, of adenosine-5'-diphosphoric acid di-n-butyl ester At least 0.02% by weight, preferably 0.02 to 1.5% by weight, in particular 0.08% by weight, of adenosine-5'-monophosphoric acid n-butyl ester.

The amounts, which are listed by way of example, of tyrosine derivatives and adenosine compounds to be added to the sunscreen product according to the invention may vary depending on whether one active substance and one activator or mixtures of active substances and mixtures of activators are present. The additions of the tyrosine derivatives and adenosine compounds according to the invention which are not listed above by way of example can be determined theoretically on the basis of their molecular weights.

The active substances and activators described according to the invention are introduced, together with the UV filter, depending on the solubility, into aqueous and/or oily solutions for the preparation of the sunscreen products according to the invention.

Preferred examples of solvents for aqueous solutions are water, aqueous ethanol, aqueous isopropanol or aqueous glycols, or mixtures thereof. By addition of suitable emulsifiers or propellant gas it is possible for the substance combinations according to the invention also to be in the form of emulsions or gels as well as aerosols or foam.

The tyrosine derivatives having longer-chain substituents are preferably dissolved in oils. Those used for this purpose are mineral oils such as, for example, liquid paraffin, vegetable oils such as, for example, olive oil, or animal oils such as, for example, squalene. Waxes such as, for example, beeswax, or fat-soluble glycols and polyglycols are also used, as are mixtures of the oily or fat-soluble substances.

The sunscreen products according to the invention also contain further additives such as, for example: protein hydrolyzate, swelling or thickening agents, surfaceactive agents, emulsifiers, film-forming substances and perfume.

The concomitant addition of the abovementioned tyrosine derivatives and at least one of the activators described, in addition to a base containing UV filters, has not yet been employed hitherto in sunscreen products. A new, effective system has been found. The sunscreen agent according to the invention is characterized fundamentally by the text, preferably as claimed in at least one of the claims. Based on this new, fundamental knowledge, some examples of formulations of cosmetic sunscreen products containing the abovementioned combination of additives have been detailed hereinafter. The long-lasting tan depicted by the full line in the figure was found with the sunscreen product having the formulation of Example 1.

Example 1

| Sunscreen cream (most important formulation) | |
|---|---|
| Oleyl oleate | 7.0% by weight |
| Lanolin | 6.0% by weight |
| Liquid paraffin | 6.0% by weight |
| Polyvinyl alcohol | 3.0% by weight |
| Polyoxyethylene stearate | 2.6% by weight |
| Beeswax | 2.5% by weight |
| Glycerol | 2.0% by weight |
| Stearyl alcohol | 2.0% by weight |
| 2-Ethoxyethyl p-methoxycinnamate | 2.0% by weight |
| Cetyl alcohol | 1.2% by weight |
| Protein hydrolyzate | 1.0% by weight |
| 3-(4-Methylbenzylidene)camphor | 1.0% by weight |
| N—Acetyltyrosine | 0.5% by weight |
| Adenosine-5'-triphosphoric acid di-Na salt | 0.05% by weight |
| Propyl p-hydroxybenzoate | 0.4% by weight |
| Perfume | 0.4% by weight |
| Water ad | 100.0% by weight |

Example 2

| Sunscreen spray | |
|---|---|
| Isopropyl myristate | 15.0% by weight |
| Dipropylene glycol | 15.0% by weight |
| N—Acetyltyrosine ethyl ester | 0.6% by weight |
| N—Acetyltyrosine | 0.5% by weight |
| Adenosine-5'-triphosphoric acid di-Na salt | 0.1% by weight |
| 2-Ethoxyethyl p-methoxycinnamate | 4.0% by weight |
| Perfume oil | 0.6% by weight |
| Ethyl alcohol (60%) ad | 100.0% by weight |
| For the spray | |
| 45% by weight of the above mixture and | |
| 55% by weight of propellant gas are used. | |

Example 3

| Sunscreen cream | |
|---|---|
| Isopropyl myristate | 20.0% by weight |
| Glycerol monostearate | 13.0% by weight |
| Lanolin | 4.0% by weight |
| Propylene glycol | 4.0% by weight |
| 2-Ethoxyethyl p-methoxycinnamate | 3.0% by weight |
| Protein hydrolysate | 1.0% by weight |
| N—Acetyltyrosine ethyl ester | 0.7% by weight |
| Adenosine-5'-triphosphoric acid di-Na salt | 0.03% by weight |
| Adenosine-5'-diphosphoric acid di-Na salt | 0.04% by weight |
| Sodium hydrogen phospate | 0.01% by weight |
| Propyl p-hydroxybenzoate | 0.3% by weight |
| Sodium lauryl sulfate | 0.1% by weight |
| Perfume oil | 0.5% by weight |
| Water ad | 100.0% by weight |

Example 4

| Sunscreen cream | |
|---|---|
| Vaseline | 30.0% by weight |
| Sesame oil | 13.0% by weight |
| Beeswax | 5.0% by weight |
| Sorbitan sesquioleate | 4.0% by weight |
| 2-Ethoxyethyl p-methoxycinnamate | 3.0% by weight |
| Liquid paraffin | 3.0% by weight |
| Protein hydrolyzate | 1.0% by weight |
| N—Acetyltyrosine ethyl ester | 0.7% by weight |
| Adenosine-5'-diphosphoric acid di-Na salt | 0.06% by weight |
| Sodium hydrogen phosphate | 0.015% by weight |
| Propyl p-hydroxybenzoate | 0.3% by weight |
| Perfume oil | 0.4% by weight |
| Water ad | 100.0% by weight |

Example 5

| Sunscreen oil | |
|---|---|
| Olive oil | 20.0% by weight |
| Polypropylene glycol P2000 | 15.0% by weight |
| 2-Ethoxyethyl p-methoxycinnamate | 4.0% by weight |
| N—Palmitoyltyrosine palmityl ester | 3.0% by weight |
| Adenosine-5'-diphosphoric acid di-n-butyl ester | 0.1% by weight |
| Propyl p-hydroxybenzoate | 0.4% by weight |
| Perfume | 0.5% by weight |
| Liquid paraffin | 57.0% by weight |

I claim:

1. A cosmetic sunscreen product for the face and body, which comprises at least one tyrosine derivative of the formula

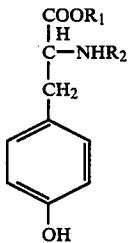

wherein $R_1$ is H or $CH_3—(CH_2)_x$, with x being an integer from 1 to 20 and $R_2$ is $CH_3CO$ or $CH_3—(CH_2)_yCO$, with y being an integer from 1 to 20.

2. A cosmetic sunscreen product for the face and body as claimed in claim 4, wherein

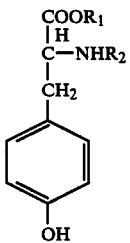

$R_1$ is H, ethyl, myristyl, palmityl or stearyl, and $R_2$ is acetyl, myristoyl, palmitoyl or stearoyl.

3. A cosmetic sunscreen product for the face and body, which comprises at least one tyrosine derivative and an activator which is at least one member selected from the group consisting of:

(i) an alkali metal salt of adenosine-5'-triphosphoric acid of the formula

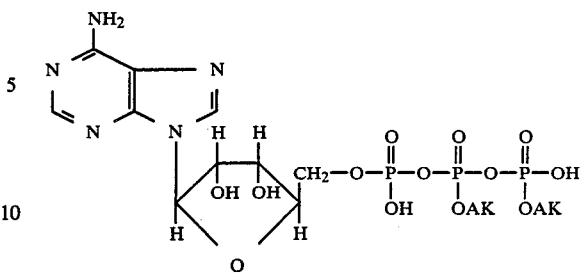

(ii) an equimolar mixture of an alkali metal dihydrogen phosphate and the alkali metal salt of adenosine-5'-diphosphoric acid of the formula

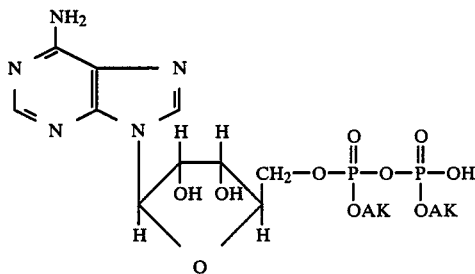

(iii) a mixture of two equivalents of an alkali metal dihydrogen phosphate and one equivalent of the alkali metal salt of adenosine-5'-monophosphoric acid of the formula

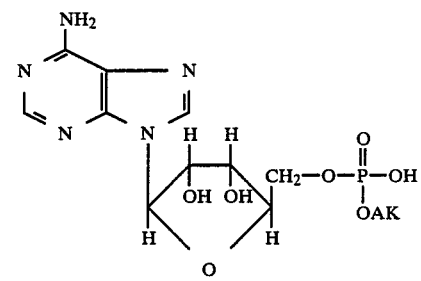

(iv) an alkaline earth metal salt of adenosine-5'-triphosphoric acid of the formula

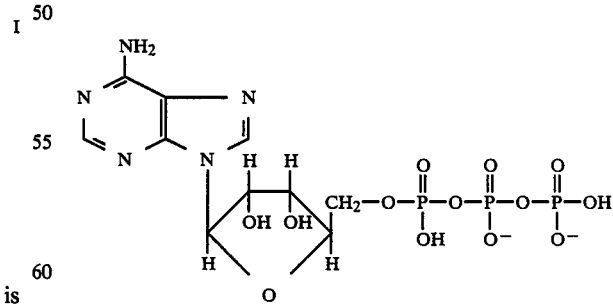

$EAK^{2+}$ (v) an equimolar mixture of an alkaline earth metal hydrogen phosphate and the alkaline earth metal salt of adenosine-5'-diphosphoric acid of the formula

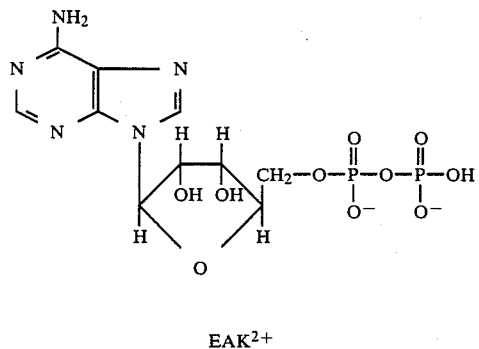

EAK²⁺

(vi) an equimolar mixture of an alkaline earth metal hydrogen phosphate and the alkaline earth metal salt of adenosine-5'-monophosphoric acid of the formula

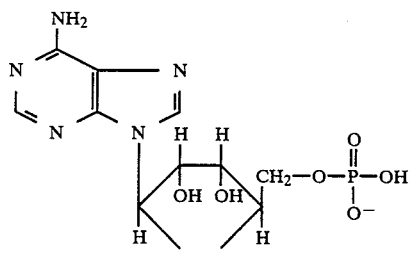

½ EAK²⁺

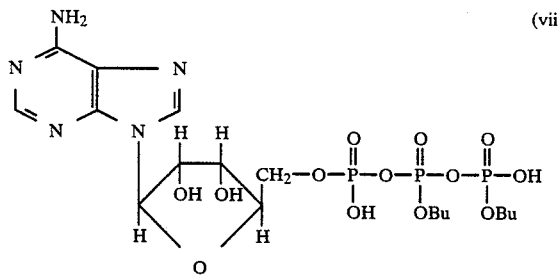

(vii)

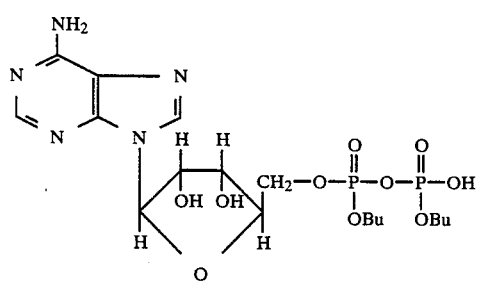

(viii)

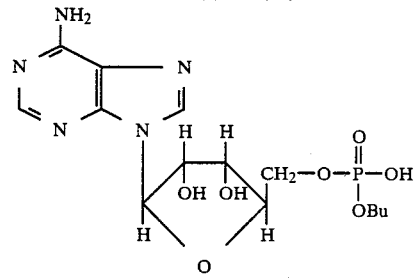

(ix)

wherein AK is an alkali metal, EAK is an alkaline earth metal, and Bu is butyl.

4. The sunscreen of claim 3, wherein said tyrosine derivative has the formula

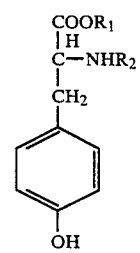

wherein $R_1$ is H or $CH_3-(CH_2)_x$, with x being an integer from 1 to 20 and $R_2$ is $CH_3CO$ or $CH_3-(CH_2)_yCO$, with y being an integer from 1 to 20.

5. A cosmetic sunscreen product for the face and body as claimed in claim 4, wherein said activator is at least one member selected from the group consisting of an alkali metal salt of adenosine-5'-triphosphoric acid of the formula

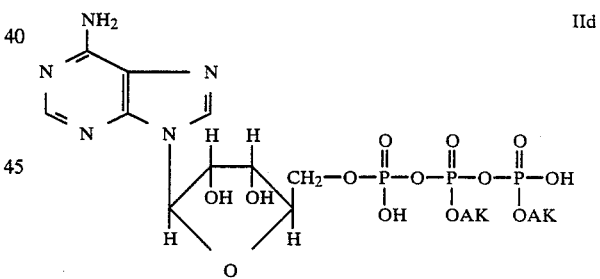

IId in which AK is an alkali element, and an equimolar mixture of an alkali metal hydrogen phosphate and the alkali metal salt of adenosine-5'-diphosphoric acid of the formula

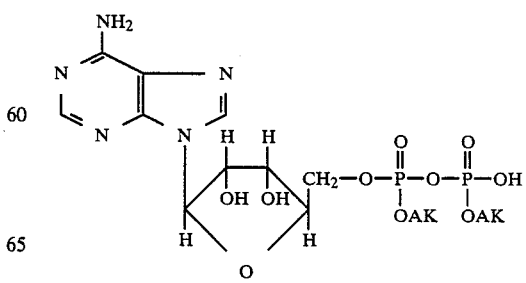

IIe in which AK is an alkali element.

6. A cosmetic sunscreen product for the face and body as claimed in claim 5, wherein said tyrosine derivative is one or more members selected from the group consisting of N-acetyltyrosine and N-acetyltyrosine ethyl ester and said alkali metal is sodium.

7. A cosmetic sunscreen product for the face and body as claimed in claim 4, which contains at least 0.3% by weight of said tyrosine derivative 8. A cosmetic sunscreen product for the face and body as claimed in claim 7, which contains at least 0.3% by weight of N-acetyltyrosine.

9. A cosmetic sunscreen product for the face and body as claimed in claim 7, which contains at least 0.4% by weight of N-acetyltyrosine ethyl ester.

10. A cosmetic sunscreen product for the face and body as claimed in claim 7, which contains at least 1.0% by weight of N-myristoyltyrosine.

11. A cosmetic sunscreen product for the face and body as claimed in claim 7, which contains at least 1.0% by weight of N-myristoyltyrosine myristyl ester.

12. A cosmetic sunscreen product for the face and body as claimed in claim 7, which contains at least 1.0% by eight of N-palmitoyltyrosine.

13. A cosmetic sunscreen product for the face and body as claimed in claim 7, which contains at least 1.0% by weight of N-palmitoyltyrosine palmityl ester.

14. A cosmetic sunscreen product for the face and body as claimed in claim 7, which contains at least 1.0% by weight of N-stearoyltyrosine.

15. A cosmetic sunscreen product for the face and body as claimed in claim 7, which contains at least 1.0% by weight of N-stearoyltyrosine stearyl ester.

16. A cosmetic sunscreen product for the face and body as claimed in claim 7, which contains at least 0.3% by weight of a mixture of N-acetyltyrosine and N-acetyltyrosine ethyl ester.

17. A cosmetic sunscreen product for the face and body as claimed in claim 4, which contains at least 0.01% by weight of said activator.

18. A cosmetic sunscreen product for the face and body as claimed in claim 17, which contains at least 0.01% by weight of adenosine-5'-triphosphoric acid disodium salt.

19. A cosmetic sunscreen product for the face and body as claimed in claim 17, which contains at least 0.015% by weight of a mixture of adenosine-5'-diphosphoric acid disodium salt and sodium hydrogen phosphate in the mixing ratio by weight of 4:1.

20. A cosmetic sunscreen product for the face and body as claimed in claim 17, which contains at least 0.015% by weight of a mixture of adenosine-5'-monophosphoric acid sodium salt and sodium hydrogen phosphate in the molar ratio of 1:2.

21. A cosmetic sunscreenproduct for the face and body as claimed in claim 17, which contains at least 0.02% by weight of adenosine-5'-triphosphoric acid di-n-butyl ester.

22. A cosmetic sunscreen product for the face and body as claimed in claim 17, which contains at least 0.02% by weight of adenosine-5'-diphosphoric acid di-n-butyl ester.

23. A cosmetic sunscreen product for the face and body as claimed in claim 17, which contains at least 0.02% by weight of adenosine-5'-monophosphoric acid n-butyl ester.

24. A cosmetic sunscreen product for the face and body as claimed in claim 17, which contains at least 0.01% by weight of adenosine-5'-triphosphoric acid disodium salt and wherein said tyrosine derivative is at least one member selected from the group consisting of N-acetyltyrosine and N-acetyltyrosine ethyl ester.

25. A cosmetic sunscreen product for the face and body as claimed in claim 17, which contains at least 0.06% by weight of a mixture of adenosine-5'-diphosphoric acid disodium salt and sodium hydrogen phosphate in the mixing ratio by weight of 4:1 and wherein said tyrosine derivative is at least one member selected from the group consisting of N-acetyltyrosine and N-acetyltyrosine ethyl ester.

26. A cosmetic sunscreen product for the face and body as claimed in claim 14, which is in the form of a solution in a solvent selected from the group consisting of water, aqueous ethanol, aqueous isopropyl alcohol and aqueous glycols.

27. A cosmetic sunscreen product for the face and body as claimed in claim 4, which is in the form of a liquid emulsion or gel and further comprises suitable solvents.

28. A cosmetic sunscreen product for the face and body as claimed in claim 4, which further comprises one or more members selected from the group consisting of mineral oils, vegetable oils, animal oils, waxes, and fat-soluble glycols and polyglycols.

29. A cosmetic sunscreen product for the face and body as claimed in claim 4, which further comprises at least one member of the group consisting of swelling or thickening agents, protein hydrolyzate, surface-active agents, film-forming substances, perfume, and emulsifiers.

30. The sunscreen of claim 4, which further comprises a UV-filter.

31. The sunscreen of claim 4, which is in the form of an aerosol or foam and further comprises a propellant gas.

* * * * *